(12) United States Patent
Lorge et al.

(10) Patent No.: US 10,822,707 B2
(45) Date of Patent: Nov. 3, 2020

(54) DEVICE FOR THE PRODUCTION OF HYDROGEN GAS

(71) Applicant: H2WIN S.A., Nivelles (BE)

(72) Inventors: Philippe Lorge, Nivelles (BE); Claire Remacle, Visé (BE); Stéphanie Gerin, Villers le Bouillet (BE); Nathalie Job, Vaux-sous-Chèvremont (BE); Fabrice Franck, Liège (BE); Giuseppe Caldarella, Ans (BE); Bart Ghysels, Laeken (BE); Damien Godaux, Seraing (BE); Pierre Cardol, Verviers (BE)

(73) Assignee: H2WIN S.A., Nivelles (BE)

( * ) Notice: Subject to any disclaimer, the term of this patent is extended or adjusted under 35 U.S.C. 154(b) by 0 days.

(21) Appl. No.: 16/079,303

(22) PCT Filed: Feb. 17, 2017

(86) PCT No.: PCT/EP2017/053651
§ 371 (c)(1),
(2) Date: Aug. 23, 2018

(87) PCT Pub. No.: WO2017/144367
PCT Pub. Date: Aug. 31, 2017

(65) Prior Publication Data
US 2019/0048478 A1 Feb. 14, 2019

(30) Foreign Application Priority Data
Feb. 23, 2016 (BE) .................................. 2016/5124

(51) Int. Cl.
*C25B 1/10* (2006.01)
*C25B 9/10* (2006.01)
*G01N 33/00* (2006.01)

(52) U.S. Cl.
CPC .................. *C25B 1/10* (2013.01); *C25B 9/10* (2013.01); *G01N 33/005* (2013.01); *Y02E 60/366* (2013.01)

(58) Field of Classification Search
CPC ... C25B 1/02–1/12; C25B 9/10; Y02E 60/366
See application file for complete search history.

(56) References Cited

U.S. PATENT DOCUMENTS

2006/0151332 A1   7/2006 Stull et al.
2008/0282653 A1* 11/2008 Tempelman ........... A61G 11/00
                                                                55/385.2

(Continued)

OTHER PUBLICATIONS

Vincent et al. Electricity from low-level H2 in still air—an ultimate test for an oxygen tolerant hydrogenase. ChemComm. 5033-5035. Nov. 2006. (Year: 2006).*

(Continued)

*Primary Examiner* — Ciel P Contreras
(74) *Attorney, Agent, or Firm* — Hanley, Flight and Zimmerman, LLC

(57) ABSTRACT

This invention concerns a device for dissociating an aqueous phase to generate hydrogen gas, said device comprising: a first zone comprising said aqueous phase, a means of electron capture, a means for reducing protons, and an energy source, said device being characterized in that said means for proton reduction is a proton exchange interface with a front side facing said means of electron capture, and a back side, with only said back side of said proton exchange interface bearing at least one catalyst and/or at least one catalytic system.

15 Claims, 3 Drawing Sheets

(56) References Cited

U.S. PATENT DOCUMENTS

| | | | | |
|---|---|---|---|---|
| 2013/0015076 | A1* | 1/2013 | Yoshida | C25B 1/02 |
| | | | | 205/340 |
| 2013/0256152 | A1 | 10/2013 | Creeth | |
| 2014/0246304 | A1* | 9/2014 | Debe | C25B 11/04 |
| | | | | 204/192.15 |
| 2015/0129431 | A1* | 5/2015 | Winther-Jensen | C25B 1/04 |
| | | | | 205/630 |
| 2015/0240368 | A1 | 8/2015 | Iacopetti et al. | |
| 2015/0321929 | A1* | 11/2015 | Legzdins | C25B 9/08 |
| | | | | 205/620 |

OTHER PUBLICATIONS

International Searching Authority, "International Search Report and Written Opinion," issued in connection with PCT Patent application No. PCT/EP2017/053651, dated Apr. 5, 2017, 15 pages.

Hannah S. Shafaat et al., [NiFe] hydrogenases: A common active site for hydrogen metabolism under diverse conditions, Biochimica et Biophysica Acta 1827 (2013) 986-1002, 17 pages.

K. Rezaei, "Effects of Water on Enzyme Performance with an Emphasis on the Reactions in Supercritical Fluids", Critical Reviews in Biotechnology, 27:183-195, 2007, 14 pages.

Zaks et al., "The Effect of Water on Enzyme Action in Organic Me," The Journal of Biological Chemistry, vol. 263, No. 17, Jun. 15, 1988, 5 pages.

\* cited by examiner

DEVICE FOR THE PRODUCTION OF HYDROGEN GAS

This patent is a nationalization of International Patent Application PCT/EP2017/053651, which was filed Feb. 17, 2017 and titled "Dispositif pour la production d'hydrogene gazeux" ("Device for the production of gaseous hydrogen"), which claims priority to Belgian Patent Application BE 2016/5124, which was filed on Feb. 23, 2016 and titled "Dispositif pour la production d'hydrogene gazeux", both of which are hereby incorporated by reference in their entireties.

This invention concerns a device for dissociating an aqueous phase to generate hydrogen gas, said device comprising:
- a first zone comprising said aqueous phase,
- a means of electron capture,
- a means for reducing protons, and
- an energy source set up to apply an energy potential, e.g. an electrical potential, between said means of electron capture and said means for reducing protons to generate oxygen gas, electrons and protons in an oxidation reaction in said aqueous phase that takes place at said means of electron capture, said means for reducing protons being set up to carry out a reduction reaction on said protons by said electrons in order to generate hydrogen gas.

In the sense of this invention, the term "aqueous phase" means a phase containing only water or any phase containing water with at least one additive, e.g. an electrolyte (buffer), a mediator of electron transport or an electron acceptor.

The first aim of developing such devices is to be able to provide a storable energy vector from an energy source, in particular from an electrical energy source, while at the same time trying to minimise the amount of energy input (in particular the input of electrical energy) required to make the device work.

Such a device is known from the background art and is used to obtain, using an electrical energy source and water, hydrogen in the form of gas ($H_{2\ gas}$). More particularly, such a device allows the generation of hydrogen gas by carrying out (1) an oxidation reaction on an aqueous phase (solution) that gives rise to the release of oxygen gas ($O_{2\ gas}$), electrons ($e^-$) and protons ($H^+$), and (2) a reduction reaction in which said protons ($H^+$) are reduced by said electrons ($e^-$), this reaction generating hydrogen in gaseous form ($H_{2\ gas}$).

In such a cell or device, oxidation of the aqueous phase (solution) typically proceeds at an anode comprising an electrochemical interface (e.g. made of carbon) which mediates the dissociation of water molecules under the effect of electrical energy input into the device by the electrical energy source, i.e. under the effect of application of an electrical potential between said means of electron capture and said means for reducing protons.

The dissociation of water molecules proceeds according to the following reaction:

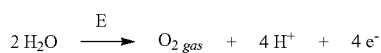

in which E corresponds to the electrical energy input into the device, $H_2O$ is water, $H^+$ represents a proton and $e^-$ represents an electron.

In this first reaction, the input of sufficient energy makes it possible to generate oxygen ($O_{2\ gas}$), protons ($H^+$) and electrons ($e^-$) by dissociating water molecules. Possibly, electrons produced in the aqueous solution by the dissociation of water molecules could ultimately be taken up by an electron mediator (acceptor) (e.g. 2,5-dichloro-1,4-benzoquinone or DCBQ) that transports them to the means of electron capture, i.e. an anode. When the anode is electrically connected to a cathode (i.e. a means for reducing protons) composed of an electrochemical interface (e.g. made of platinum and/or carrying hydrogenase-like enzymes), the electrons are transported to the latter. In parallel, the protons too diffuse through the aqueous phase to the cathode. It is at the cathode that the electrons and protons generated by the dissociation of water molecules under the effect of an applied electrical potential, finally combine to generate hydrogen gas in a reaction in which the protons are reduced according to a second reaction, as follows:

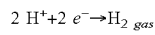

Hydrogen gas ($H_{2\ gas}$) is therefore finally obtained and can be extracted from the device with a view, by way of example, for storage.

Such a device has traditionally been made up of two electrodes, e.g. in the form of grids made of platinum or carbon, submerged in the same aqueous solution and connected to one another, e.g. via a potentiostat. With such an already known device for dissociating water molecules in which the electrodes take, for example, the form of grids, usually made of platinum and/or carbon, this potentiostat (or any other suitable apparatus) must always supply a significant, non-negligible amount of energy potential to generate hydrogen gas ($H_{2\ gas}$). In practice, it appears that with devices currently known from the background art, such additional energy potential is indispensable to the production of hydrogen gas. More particularly, such additional energy potential is indispensable for transfer to the cathode of electrons produced at the anode, thereby allowing the reduction of the protons $H^+$ by the electrons $e^-$ to generate hydrogen gas at the cathode.

It turns out that electrons from the water are confronted with a transmission cascade and various interfaces before they can reach the anode and then the cathode, each of these transmissions and each of these interfaces consuming some part of the electron's energy.

From all this, it unfortunately emerges that, with current devices, a significant amount of additional energy potential always has to be supplied to give the electrons enough energy to overcome all these transmissions and all these interfaces to reach the cathode (the means for proton reduction) and there reduce protons to generate hydrogen gas. It follows that overall energy balance and overall energy yield are not optimised in these devices.

There is therefore a real need for a device to generate hydrogen gas which minimises the amount of energy that needs to be input, e.g. the input of electrical energy, or that can at least considerably cut down the energy potential required to generate hydrogen gas.

To overcome this problem, the invention provides for a device to dissociate an aqueous phase and generate hydrogen gas as indicated at the beginning, said device being characterised in that said means for proton reduction is a proton exchange interface with a front side facing said means of electron capture, and a back side, with only said back side of said proton exchange interface bearing at least one catalyst and/or at least one catalytic system.

In the sense of this invention, the terms "catalyst" and "catalytic system" mean any agent or set of agents that can catalyse an oxidation and/or reduction reaction.

In the sense of this invention, the phrase "only said back side of said proton exchange interface bearing at least one catalyst and/or at least one catalytic system" means that only the back side of the proton exchange interface is doped with at least one catalyst and/or at least one catalytic system.

According to the invention, the proton exchange interface (e.g. a membrane), also referred to as polymer electrolyte membrane (PEM), is an interface that allows the conduction of protons without allowing the passage of gases like bimolecular oxygen or hydrogen.

Surprisingly, in the context of this invention, it has been shown that such a device with a means of proton reduction in the form of a proton exchange interface with only its back side bearing at least one catalyst and/or at least one catalytic system, makes it possible to considerably reduce the energy potential (e.g. electrical potential) that has to be applied to the device. In practice, it was discovered that the device according to the invention reduces the energy potential that has to be applied to the device to generate hydrogen gas by almost one volt.

More particularly, in the context of this invention it was determined that less energy potential needs to be applied when protons reaching the proton exchange interface are taken up at the latter's front side and then transported across the proton exchange interface to reach its back side where the protons are directly reduced as long as only the back side of this proton exchange interface bears at least one catalyst and/or at least one catalytic system.

Preferably according to the invention, said means of electron capture may or may not include at least one catalyst and/or at least one catalytic system.

Advantageously according to the invention, said means of electron capture is a proton exchange interface or a carbon grid.

Preferably according to the invention, said at least one catalyst and/or said at least one catalytic system contains hydrogenase-like enzymes and/or particles of platinum. It has been determined that hydrogenase-like enzymes, in addition to being cheaper than platinum, can not only handle more electrons per unit time (per second) but also somewhat cuts down the energy potential required by the device to generate hydrogen gas. The above-mentioned hydrogenase-like enzymes could be produced by synthesis rather than extracted from naturally-occurring organisms.

Advantageously according to the invention, said proton exchange interface constitutes a separator between said first zone containing the aqueous phase and a second non-aqueous phase.

In the sense of this invention, the term "second non-aqueous phase" means for example a zone comprising a solid phase or a non-aqueous liquid phase or a zone with no liquid phase.

Preferably according to the invention, said separator does not let either said liquid phase or gases (in particular $O_2$) pass but it does let protons through. In one embodiment, such a separator according to the invention ensures that the reduction reaction only proceeds in the non-aqueous zone. In this case, it is planned according to the invention that the front side of the separator (the interface, e.g. in the form of a membrane with both a front side and a back side) is in contact with the aqueous phase or in direct contact with the anode and therefore positioned on the first aqueous zone side. Thus it is planned that the back side that is doped with catalyst (e.g. carbon or platinum) is positioned on the second non-aqueous zone side. The reaction in which protons are reduced by electrons to generate hydrogen gas only proceeds at the back side of the interface (membrane) and therefore exclusively on the second non-aqueous zone side. This is possible if, as stated above, the separator (membrane) does not let the aqueous phase through but lets protons pass into the second non-aqueous zone with protons only reduced at the back side of this separator (interface) and therefore in the second non-aqueous zone. In the context of this invention, it has been determined that reducing protons in a non-aqueous zone optimises intensity (the magnitude/amplitude of the current) when a given energy potential is applied to the system.

Preferably according to the invention, a means of contact is present on said means of electron capture and/or on said means for proton reduction. For example, carbon fabric is planned to provide optimal electrical contact between said means of electron capture and said means for proton reduction, e.g. via a potentiostat.

Preferably according to the invention, said aqueous phase is a phase containing only water or any phase containing water with at least one additive, e.g. an electrolyte, a mediator of electron transport or an electron acceptor.

Preferably according to the invention, said aqueous phase also contains a mediator of electron transport or an electron acceptor. Possibly, said mediator of electron transport or said electron acceptor is in the form of carbon nanotubes or ferricyanide.

Advantageously according to the invention, said aqueous phase has a pH of between 0.1 and 10, preferably between 6 and 7.

Preferably, the device to dissociate an aqueous phase to generate hydrogen gas according to the invention also includes an additional device to recover and remove the gas. For example, this could take the form of a device that ensures the flow of nitrogen through said second non-aqueous zone in order to recover and remove gases present in said second non-aqueous zone, notably the hydrogen gas produced by the reduction of protons in this second non-aqueous zone.

Preferably, the device to dissociate an aqueous phase to generate hydrogen gas according to the invention also includes an additional device to detect hydrogen gas.

Other embodiments of the device according to the invention are described in appended Claims.

Another object of the invention is a process for producing hydrogen gas with a device according to the invention from an aqueous phase and an energy source, said process comprising the following steps application of an energy potential between a means of electron capture and a proton exchange interface with a front side facing said means of electron capture and a back side bearing at least one catalyst and/or at least one catalytic system, to generate oxygen gas, electrons and protons at said means of electron capture, in a reduction reaction on said aqueous phase, and capture of said protons at said proton exchange interface with a front side facing said means of electron capture and a back side with at least one catalyst and/or at least one catalytic system, so said protons are reduced to gaseous hydrogen in a reduction reaction on said protons by said electrons at said back side of said proton exchange interface.

Other embodiments of the process according to the invention are described in appended Claims.

The invention also concerns use of a device according to the invention to produce hydrogen gas from an aqueous phase and an energy source.

Other uses of a device according to the invention are described in appended Claims.

Other characteristics, details and advantages of the invention will emerge from the description hereafter which is non-limiting and makes reference to the appended Figures.

The same components are labelled in the same way in the different Figures.

Figure 1:
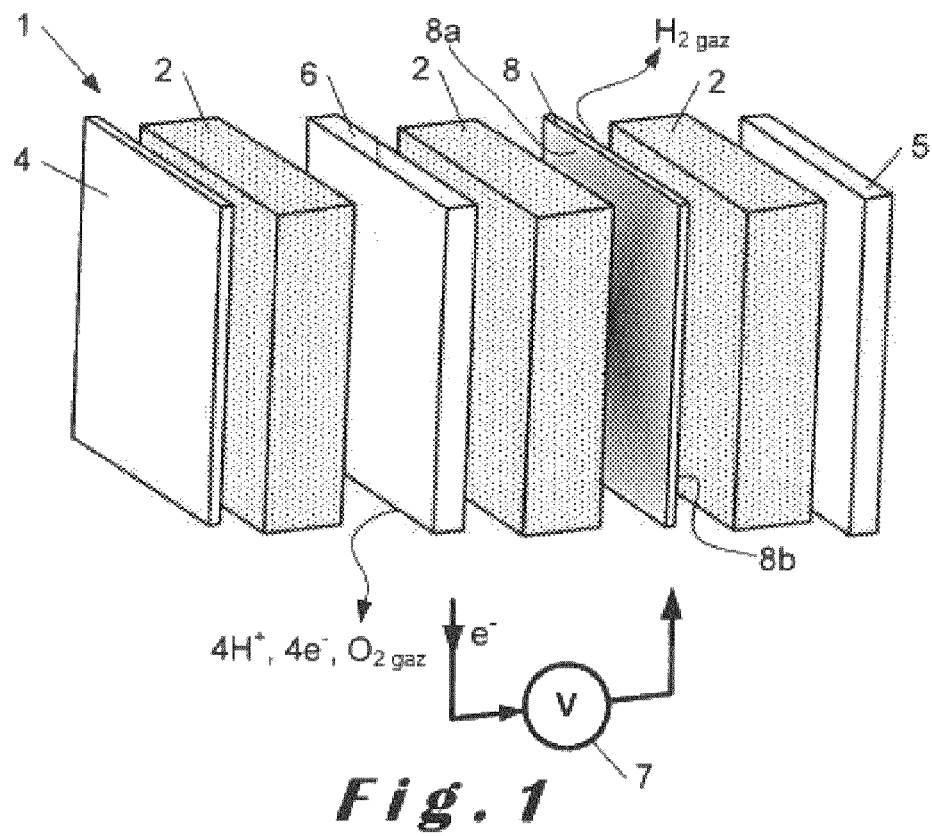
FIG. 1 is an exploded view of a device according to the invention to generate hydrogen gas from an aqueous phase and an energy source, in this case from an aqueous phase and an electrical energy source.

FIG. 1 illustrates a device 1 according to the invention that produces hydrogen gas ($H_{2\ gas}$) from an aqueous phase 2 and an electrical energy source 7. This device 1 has a front wall 4 and a back wall 5, e.g. walls 4, 5 made of a suitable polymer. Of course, the device 1 also has top, bottom and side walls that, together with the front and back walls, create a watertight device (generator).

The aqueous phase 2 bathes an anode 6 (e.g. a carbon anode 6) connected through a potentiostat 7 (an electrical energy source) to an interface in the form of a proton exchange membrane 8 with a front side 8a facing said means of electron capture 6 and its back side 8b containing at least one catalyst and/or at least one catalytic system, with the membrane (interface) 8 also submerged in the same aqueous phase 2. When an energy potential is applied between anode 6 and membrane (interface) 8, an oxidation reaction on the aqueous phase 2 proceeds at the anode 6 to produce oxygen gas ($O_{2\ gas}$), electrons (4 $e^-$) and free protons (4 $H^+$). More particularly, the membrane (interface) 8 has a front side 8a in contact with the aqueous phase 2 and a back side 8b (also in contact with aqueous phase 2) which is doped with platinum so that it can act as a cathode. The reaction in which the protons ($H^+$) are reduced by electrons ($e^-$) to generate hydrogen gas ($H_{2\ gas}$) only proceeds on the back side 8b of the membrane (interface) 8.

Preferably, aqueous phase 2 contains a mediator of electron transport or electron acceptor (e.g. DCBQ) that takes the electrons to the anode 6 in such a way that, since the latter is electrically connected to the cathode 8 via a potentiostat 7, the electrons can reach the membrane (interface) 8 and there combine with protons which will also have reached the membrane (interface) 8 via the aqueous phase 2. On the back side of the membrane (cathode) 8, a reduction reaction proceeds in which protons $H^+$ are reduced by electrons $e^-$ to generate hydrogen gas ($H_{2\ gas}$). Possibly, carbon fabric (Gas Diffusion Layer—GDL) could be placed on the back side 8b (facing wall 5) of the membrane (interface) 8 (doped and acting as a cathode) to create an electrical contact layer between membrane (cathode) 8 and potentiostat 7.

Figure 2:
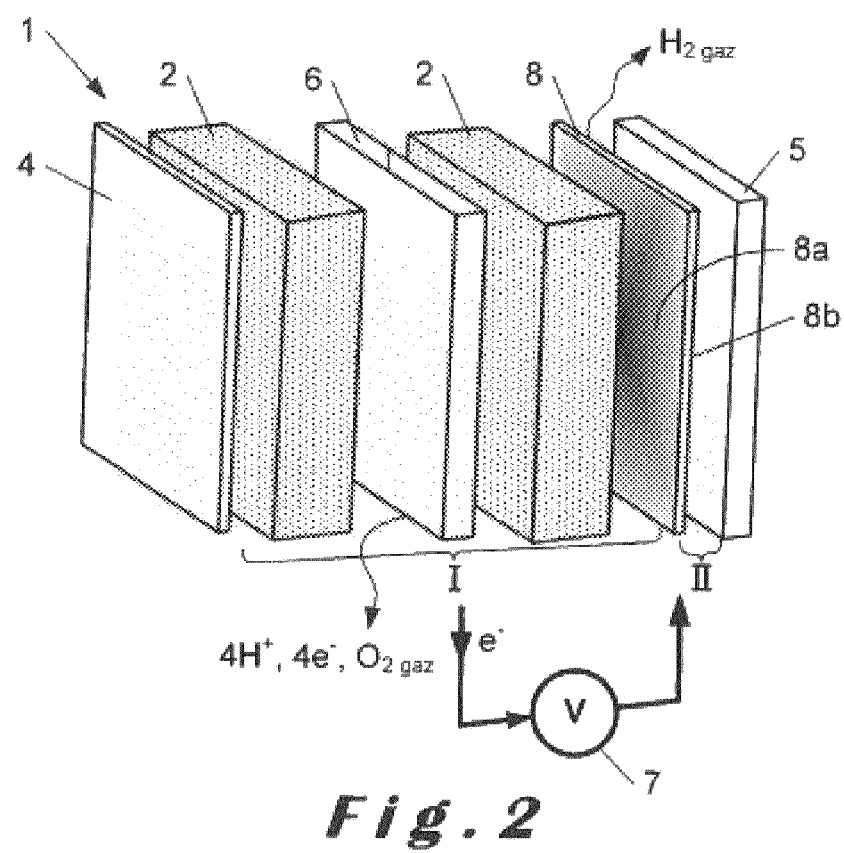
FIG. 2 is an exploded view of another device according to the invention to generate hydrogen gas from an aqueous phase and an energy source, in this case from an aqueous phase and an electrical energy source.

FIG. 2 illustrates a device 1 according to the invention that produces hydrogen gas ($H_{2\ gas}$) from an aqueous phase 2 and an electrical energy source 7. This device 1 according to the invention as illustrated in FIG. 2 has a first aqueous zone I and a second non-aqueous zone II. According to this embodiment, a membrane (interface) 8 in the form of a PEM-type membrane 8 doped with platinum and carbon constitutes a separator between the first aqueous zone I and the second non-aqueous zone II. Doping the membrane (interface) 8 with carbon and platinum turns it into a cathode. This separator in the form of a membrane (interface) 8 blocks passage of both the aqueous phase 2 and gases but lets protons ($H^+$) through from said aqueous zone I into said non-aqueous zone II. More particularly, this membrane (separator) 8 has a front side 8a in contact with the aqueous phase 2 and faces towards the side of the first aqueous zone I. This membrane (separator) 8 also has a back side 8b which is doped with platinum so that it can act as a cathode, and said back side 8b faces onto the side of the second non-aqueous zone II. According to this embodiment, the reaction in which the protons ($H^+$) are reduced by electrons ($e^-$) to generate hydrogen gas ($H_{2\ gas}$) only proceeds on the back side 8b of the separator (interface) and therefore exclusively on the non-aqueous zone II side. Possibly, carbon fabric (Gas Diffusion Layer—GDL) could be placed on the back side 8b (facing wall 5) of the membrane (interface) 8 (doped and acting as a cathode) to create an electrical contact layer between membrane (cathode) 8 and potentiostat 7.

Figure 3:
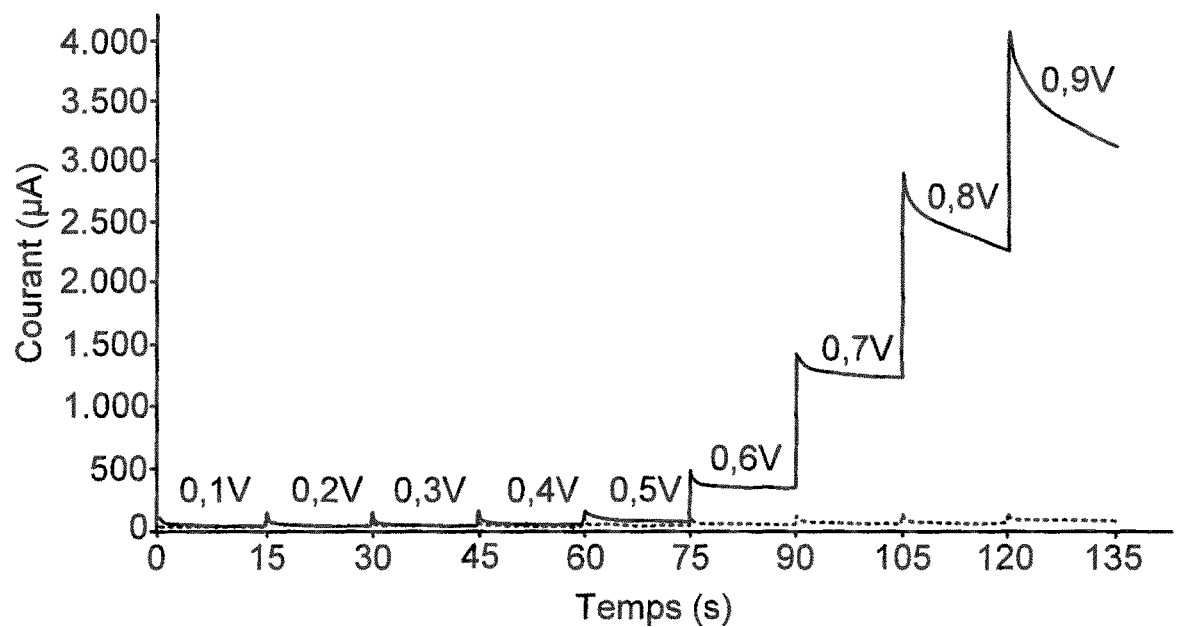
FIG. 3 shows a graph of results recorded in ampero-multivoltage measurements (from 0.1 V to 0.9 V) for devices according to the invention (including a doped proton exchange interface—continuous line) as illustrated in FIGS. 1 and 2 compared with a background art device (including an undoped proton exchange interface and a platinum grid—broken line).

FIG. 3 shows results of ampero-multivoltage measurements (from 0.1 to 0.9 V) for devices according to the invention as illustrated in FIGS. 1 and 2 (continuous line—devices according to the invention with a membrane/interface doped with platinum), compared to measurements made in the same conditions with a background art device containing an undoped membrane and a platinum grid (broken line—background art). As can be seen, with devices according to the invention, a current is measured between the anode and the membrane (interface/cathode) when a potential of 0.6 V is applied. In contrast, no current passes between anode and cathode in a background art device, even when a higher potential is applied, e.g. 0.9 V. Moreover, for devices according to the invention, the current measured rises considerably for applied potentials of 0.7 V, 0.8 V and 0.9 V.

These comparative experiments show that devices according to the invention with a means of proton capture in the form of a proton exchange interface with only its back side bearing at least one catalyst and/or at least one catalytic system, affords a better energy yield than a device known to the background art.

For these comparative experiments, the aqueous phase 2 contained DCBQ (0.75 mM) and a buffer (NaCl 50 mM, MES 20 mM, MgCl 2 mM). Moreover, for the embodiment illustrated in FIG. 2, an extra device was included to recover and remove gases from the non-aqueous zone.

Figure 4:
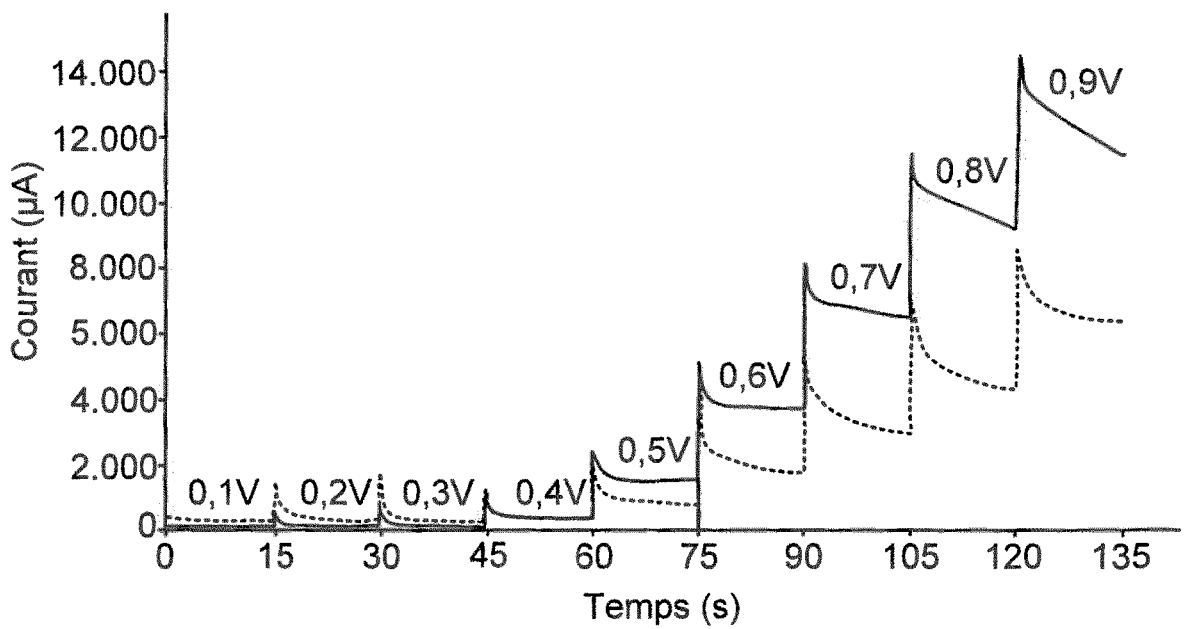
FIG. 4 shows a graph comparing results recorded in ampero-multivoltage measurements (from 0.1 V to 0.9 V) for two different devices according to the invention as illustrated in FIG. 1 (broken line) and FIG. 2 (broken line) with a doped proton exchange interface.

FIG. 4 shows a graph comparing results recorded in ampero-multivoltage measurements (from 0.1 V to 0.9 V) for devices according to the invention as illustrated in FIG. 1 (broken line) and FIG. 2 (continuous line). For each of these embodiments illustrated in FIGS. 1 and 2, a proton exchange membrane (PEM interface) doped with platinum acts as a cathode. As shown by the graph, the current (μA) is higher on the application of a given potential to the system, when the system includes a proton exchange interface doped with platinum and separating a first aqueous zone from a second non-aqueous zone (the embodiment shown in FIG. 2). In this graph, the embodiment according to FIG. 2 is compared to a device according to FIG. 1 which contains no non-aqueous zone. This shows that current intensity is optimised in the embodiment of the invention illustrated in FIG. 2 with a non-aqueous zone in which the proton reduction reaction proceeds. This implies more intense $H_{2\ gas}$ production for a given, pre-set applied energy potential, compared with a device according to the invention without any non-aqueous zone.

Figure 5:
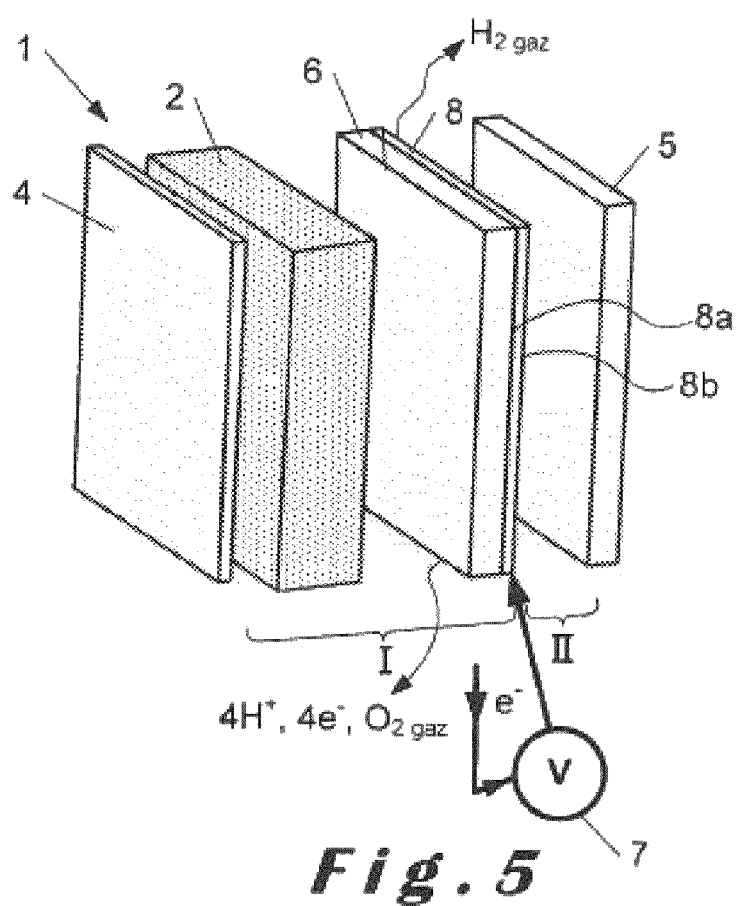
FIG. 5 is an exploded view of another device according to the invention to generate hydrogen gas from an aqueous phase and an energy source, in this case from an aqueous phase and an electrical energy source.

FIG. 5 is a view of another device according to the invention that produces hydrogen gas ($H_{2\ gas}$) from an aqueous phase 2 and an electrical energy source 7. This device 1 is identical to that illustrated in FIG. 2 apart from the fact that the membrane (interface) 8 is juxtaposed against the back side of the anode 6. The membrane (interface) 8 constitutes a separator between the first aqueous zone I and the second non-aqueous zone II, and it is doped with carbon and platinum so that it can act as a cathode. This separator in the form of a membrane 8 blocks passage of both the aqueous phase 2 and gases (in particular $O_2$) but lets protons (H+) through. More particularly, this membrane (interface) 8 has a front side 8a in direct contact with the anode 6 (because it is juxtaposed against the back side of the anode 6), and said front side faces onto the side of the first aqueous zone I. This membrane (interface) 8 also has a back side 8b which is doped with platinum so that it can act as a cathode, and said back side 8b faces onto the side of the second non-aqueous zone II. The reaction in which the protons ($H^+$) are reduced by electrons ($e^-$) to generate hydrogen gas ($H_{2\ gas}$) only proceeds in this non-aqueous zone II at the back side of the membrane 8. Possibly, carbon fabric (Gas Diffusion Layer—GDL) could be placed on the back side (facing wall 5) of the membrane (interface or separator) 8 (doped and acting as a cathode) to create an electrical contact layer between membrane (cathode) 8 and potentiostat 7.

According to this embodiment according to the invention as illustrated in FIG. 5, the reduction reaction proceeds in the non-aqueous zone II but, in addition, protons generated in the aqueous phase in the oxidation reaction are directly taken up at the membrane (interface) 8 without having to cross any aqueous phase as is the case with the embodiment according to the invention as illustrated in FIG. 2. In this case, the protons do not return into an aqueous phase again: they are directly taken up at the membrane (interface) 8 that acts as a cathode 8 in the non-aqueous zone II.

It is fully understood that this invention is in no way limited to the embodiments described above and that modifications could be made without going beyond the scope of the Claims.

The invention claimed is:

1. A device to generate hydrogen gas, the device comprising:
    a first zone including an aqueous phase;
    means for capturing electrons;
    means for reducing protons; and
    an energy source to apply an energy potential between the means for capturing electrons and the means for reducing protons to generate oxygen gas, electrons, and protons in an oxidation reaction in the aqueous phase, the oxidation reaction to occur at the means for capturing electrons;
    wherein the means for reducing protons is to carry out a reduction reaction on the protons by the electrons to generate hydrogen gas;
    wherein the means for reducing protons includes a proton exchange interface constituting a separator between the first zone including the aqueous phase and a second non-aqueous zone, the separator to prevent the aqueous phase from passing through from the first zone into the second non-aqueous zone, the separator to permit protons to pass through from the first zone into the second non-aqueous zone, the proton exchange interface including:
        a front side being located in the first zone and facing the means for capturing electrons; and
        a back side being located in the second non-aqueous zone and bearing at least one catalyst and/or at least one catalytic system containing hydrogenase enzymes.

2. The device according to claim 1, wherein the means for capturing electrons includes at least one catalyst and/or at least one catalytic system.

3. The device according to claim 1, wherein the means for capturing electrons includes a proton exchange interface.

4. The device according to claim 1, wherein the means for capturing electrons includes a carbon grid.

5. The device according to claim 1, wherein the at least one catalyst and/or the at least one catalytic system contains particles of platinum.

6. The device according to claim 1, wherein the separator is to prevent gases from passing through the first zone.

7. The device according to claim 1, further including a means for contacting on the means for capturing electrons and/or on the means for reducing protons.

8. The device according to claim 1, wherein the aqueous phase is a phase containing only water.

9. The device according to claim 1, wherein the aqueous phase is a phase containing water with at least one additive.

10. The device according to claim 1, wherein the aqueous phase is a phase containing a mediator of electron transport or an electron acceptor.

11. The device according to claim 1, wherein the aqueous phase has a pH of between 0.1 and 10.

12. The device according to claim 1, wherein the aqueous phase has a pH of between 6 and 7.

13. The device according to claim 1, further including a gas remover.

14. The device according to claim 1, further including a hydrogen gas detector.

15. A method for producing hydrogen gas from an aqueous phase and an energy source with a device according to claim 1, the method comprising:
    applying an energy potential between the means for capturing electrons and the proton exchange interface;
    capturing the protons at the proton exchange interface; and
    reducing the protons to gaseous hydrogen in a reduction reaction on the protons by the electrons at the back side of the proton exchange interface.

* * * * *